United States Patent [19]
Cho

[11] 3,947,480

[45] Mar. 30, 1976

[54] DINITRO- AND DIAMINO ARYLENE DISULFONES

[75] Inventor: Iwhan Cho, Lincoln Park, N.J.

[73] Assignee: Uniroyal, Inc., New York, N.Y.

[22] Filed: Nov. 6, 1974

[21] Appl. No.: 521,307

Related U.S. Application Data

[62] Division of Ser. No. 248,367, April 28, 1972, Pat. No. 3,859,252.

[52] U.S. Cl. .......................................... 260/397.6
[51] Int. Cl.² ...................................... C07C 147/00
[58] Field of Search ............................... 260/397.6

[56] References Cited
UNITED STATES PATENTS

| | | | |
|---|---|---|---|
| 3,503,931 | 3/1970 | Radlmann et al. | 260/78 R |
| 3,505,288 | 4/1970 | Bodesheim et al. | 260/78 R |

OTHER PUBLICATIONS

Chem. Abst. 70 114825(z) (1969)–pp "Dinitrodiphenyl ethers" Benty et al.

Primary Examiner—Stanley J. Friedman
Assistant Examiner—D. W. Robinson
Attorney, Agent, or Firm—Willard R, Sprowls

[57] ABSTRACT

Novel symmetrical dinitro- and diamino arylene disulfones. The dinitro compounds are prepared by the interaction of a disodium arylenedisulfinate and a p-halonitro-benzene. The diamino compounds may be prepared by reduction of the corresponding dinitro disulfones, as by means of stannous chloride, or by hydrogenation with the aid of a catalyst such as palladium or carbon.

4 Claims, No Drawings

DINITRO- AND DIAMINO ARYLENE DISULFONES

This is a division of application Ser. No. 248,367, filed Apr. 28, 1972, now U.S. Pat. No. 3,859,252, issued Jan. 7, 1975.

The polymers are considered to have the structure

wherein Ar is divalent aromatic structure, Ar' is phenylene, "bis-amide structure" is —NH—CO—R—CO—NH— or —CO—NH—R'—NH—CO—, R is alkylene or phenylene, and R' is phenylene or p,p'-diphenylene.

Certain of the reactive monomeric polysulfone derivatives used in these condensation reactions are themselves new compounds, namely, (1) the symmetrical dinitro polyarylene disulfones; and (2) the corresponding diamino polyarylene disulfones, made by reduction of the dinitro compounds.

Fibers, filaments, films, and molded articles of my polyamido-polysulfone thermoplastics have unusual heat resistance and exceptional flame resistance, and excellent mechanical, physical, chemical, and electrical properties. They are particularly useful for thermal and electric insulation, as well as in the automotive and aircraft industries.

BACKGROUND OF THE INVENTION

Polyamide-arylene sulfone thermoplastics are known having a single sulfonyl group in the recurring structural unit —(1) Stephens, *Journal of Polymer Science* 40, 359 (1959); (2) Stroog et al., *Journal of Polymer Science* A3, 1973 (1965); (3) Jones, *Annual Technical Conference of the Society of Plastic Engineering and Technology*, 15, 453 (1969); (4) Hill et al., U.S. Pat. Nos. 3,094,511 and 3,322,728.

Alpha, omega-dicarboxy-polymethylenedisulfones of the general structure
$HOOC(CH_2)_x$—$SO_2$—$(CH_2)_y$—$SO_2$—$(CH_2)_x COOH$ have been poly-condensed with alkylenediamines to make fiber-forming poly(disulfone)-polyamides. —Horn, *Die Makromol. Chem.e* 29, 123 (1959).

Symmetrical dimethyl polyarylene disulfones, and the corresponding dicarboxylic acids and diacid chlorides derived therefrom, are known. —S. S. Gitis et al., *Khim. Volokna*, 1971, No. 1, pages 45–47.

THE INVENTION

Polymers

My new thermoplastic high polymers are aromatic polyamide-polysulfones composed of recurring units of bis-amide moieties alternating with polarrylene disulfone moieties. They are characterized by unusually high heat resistance and flame resistance.

There are two approaches to the preparation of my polymers, leading to the formation of two configurations having different but very closely related structures. In one type of reaction the disulfone monomer carries the amide-forming amino groups, which are to be condensed with a complementary amide-forming diacidyl compound to form polymers. In the other type of reaction, the disulfone monomer carries amide-forming acid —derivative terminal groups, to be condensed with an aromatic diamine to form polymers. The complementary structures of the two types of polymers thus formed are illustrated by the following schematic sequences or —CO—, —NH—, and —$SO_2$— groups present in the recurring units of the polymer chains:

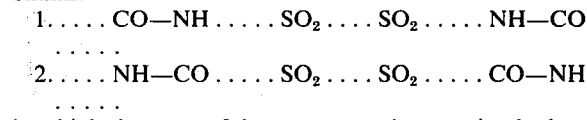

in which the rows of dots represent intervening hydrocarbon, etc., structures. In ehtier type of reaction the amide linkages formed may be of the carboxamido or of the sulfonamido type.

For use in polymerization reactions of the first type, typical di-acid chlorides and di-acid anhydrides include those of both aromatic and aliphatic diacids, wherein the acid groups are attached to m-phenylene, p-phenylene, p-bisphenylene, p,p'-oxydiphenylene, and ethylene —$CH_2CH_2$—, diethylene —$(CH_2CH_2)_2$—, triethylene —$(CH_2CH_2)_3$—, and tetraethylene —$(CH_2CH_2)_4$—. Examples below illustrate the use of various such di-acid compounds.

The aromatic diamino disulfones used, with which the di-acid compounds are to be condensed, contain two sulfonyl groups joined to an aromatic group such as m-phenylene, p-phenylene, p,p'-oxydiphenylene, p,p'-biphenylene, and 1,5-naphthylene, each sulfonyl also being joined to p-aminophenyl. These diamino disulfones may be schematically represented thus:

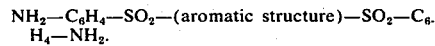

For polymerization reactions of the second type, the aromatic bis(sulfonylphenylene) compounds used carry two acidyl groups which are reactive with amines to form amides, and are designated aromatic bis(sulfonylphenyleneacidyl) compounds. These are to be interpolymerized with m-phenylenediamine or p,p'-diphenylenediamine to provide the bis-amido formations which alternate with bis-sulfone moieties in the polymer chains.

In all interpolymerization reactions of my invention, the components are used in substantially equimolar amounts. A convenient solvent medium for the reactions is N,N-dimethylacetamide. Other suitable solvents are sulfolane, with which a trialkyl amine, e.g., triethylamine or pyridine, is used as an acid scavenger, and tetramethylurea.

No catalyst is required for the reactions, which begin spontaneously upon admixture of the reactants in the solvent, with generation of some heat. Polymerization is complete after one to three hours, whereupon the polymers are recovered by precipitation in aqueous methanol, separation of solid from liquid, and drying.

The polymers are generally amorphous, and of light color in bulk, and transparent in films. In certain cases are amorphous polymer crystallizes when held at a temperature slightly above its glass transition temperature.

The following examples illustrate the preparation of polymers of my invention.

EXAMPLE I

This shows the interpolymerization of (A) 4,4'-oxybis[4-(phenylsulfonyl)aniline] and (B) isophthaloyl chloride. In 20 ml. of $P_2O_5$-dried N,N-dimethylacetamids there was dissolved 2.265 grams (0.005 mole) of A and then 1.015 grams (0.005 mole) of B. An exothermic reaction took place, the solution becoming viscous. The polymerization was continued with stirring for an additional three hours at room temperature. The solution was then poured into a methanol/water mixture and the precipitated polymer was separated out, washed with additional methanol/water, and dried at 100°C. under vacuum, yielding 2.5 grams of an off-white amorphous polymer having an intrinsic viscosity of 0.29 in dimethylformamide at 30°C.

EXAMPLE II

This shows the interpolymerization of (A) m-phenylenebis(p-sulfonylaniline) and (B) terephthaloyl chloride. to a solution of 3.88 grams (0.01 mole) of A in 40 ml. of N,N-dimethylacetamide there was added 2.03 grams(0.01 mole) of B (freshly distilled and recrystalized from n-heptane) at room temperature. Exothermic reaction took place and the solution became viscous. After two hours of stirring, the polymer was precipitated into water. The precipitate was separated by filtration, washed a few times with methanol, and dried at 180°C. under vacuum. The yeild was 5.0 grams. The I.V. value was 0.3 in dimethylformamide. Differential thermal analysis showed an exothermic transition at 280°C. indicating crystallization of the polymer.

EXAMPLE III

This shows the interpolymerization of (A) 4,4'-oxybis[4-(phenylsulfonyl)aniline] and (B) sebacoyl chloride. In 150 ml. of dry N,N-dimethylacetamide there was dissolved 10.0 grams (0.0208 mole) of A and then 5 grams (0.021 mole) of distilled B.

At the start of the polymerization, an exothermic reaction took place, resulting in the solution becoming viscous. As in the previous example, the polymerization was continued, with stirring, for an additional three hours. The polymer was then precipitated into a methanol/water mixture. If further purification is necessary, the polymer can be reprecipitated from N,N-dimethylacetamide into a methanol/water mixture. The polymer was then dried at 100°C. under vacuum, resulting in an intrinsic viscosity of 0.48 measured at room temperature in dimethylformamide. The polymer was amorphous and gave a transparent, flexible film when cast from N,N-dimethylacetamide solution. The glass transition temperature of the polymer was ca. 390°F., determined on a Perkin-Elmer differential scanning calorimeter. The I.V. in dimethylacetamide was 0.33, corresponding to a molecular weight of about 8,000.

EXAMPLE IV

This shows the interpolymerization of the same sulfonylamiline compound (A) used in Examples I and III, and (B) 4,4'-oxydiphenylene-disulonyl chloride. In 20 ml. of dry N,N-dimethylacetamide there was dissolved 1.677 grams (0.0037 mole) of A and then 1.34 grams (0.00365 mole) of B. After stirring for three hours, the polymer was precipitated into methanol/water and dried at 100°C. under vacuum. The polymer was amorphous and off-white in color. A film cast from dimethylformamide solution was brittle.

EXAMPLE V

In 10 ml. of dry N,N-dimethylacetamide there was dissolved 2.6 grams (0.0045 mole) of 4,4'-oxybis(p-phenylsulfonylbenzoyl chloride) and then 0.5 gram (0.0046 mole) of m-phenylenediamine. An exothermic reaction took place immediately, and the mixture was stirred for an additional hour. The polymer was then precipitated into methanol/water and dried at 100°C. under vacuum. The polymer was amorphous and off-white in color, and the film cast from dimethylformamide solution was brittle.

EXAMPLE VI 4,4'-Biphenylene-bis(4-sulfonylaniline), m.p., 290°C. (7 g., 0.015 mole) was dissolved in 50 ml. of dry dimethylacetamide and to it was added 3.06 g. (0.015 mole) of recrystallized isophthaloyl chloride in one portion with stirring. Exothermic reaction started immediately and the solution became viscous. The reaction was allowed to proceed for an additional 2 hours. The solution was then poured into water and the polymer precipitate was separated by filtration. The polymer was dried at 180°C. under vacuum for twelve hours. I.V. = 0.25/DMAc. The polymer showed (1) no crystallinity on x-ray diffraction, (2) had a glass transition temperature at 530°F., and (3) could be meltspun at 650°F.

POLYMER FILAMENTS

Fibers are conveniently prepared from my polymers by conventional methods, and are found to have unusually high heat resistance and flame resistance. For example, polymer prepared according to Example I was melt-spun at 660°F. to give a 40-denier filament with high spin orientation. The product was spun and wound in a single step and is a fairly tough, amorphous fiber with a tenacity of about 1.8 grams per denier. In short-term heat resistance tests, this fiber possessed good strength retention, up to its glass transition temperature of 265°C. The relative flammability of this fiber is significantly lower than that of most common textile fibers.

MONOMERS

The monomeric diamino disulfones employed in producing my polymers are themselves new compounds, as are the nitro compounds from which the diamino compounds are made. The new monomeric compounds include the following:

1. bis)nitrophenylsulfonyl)arylene compounds, e.g.,
   p-bis(P-nitrophenylsulfonyl)benzene,
   m-bis(p-nitrophenylsulfonyl)benzene,
   p,p'-bis(p-nitrophenylsulfonylphenyl) ether,
   p,p'-bis(p-nitrophenylsulfonyl)biphenyl,
   1,5-bis(p-nitrophenylsulfonyl)naphthalene.
2. bis(aminophenylsulfonyl)arylene compounds, or arylenebis(p-phenylsulfonylanilines), e.g.,
   p-phenylenebis(p-sulfonylaniline),
   m-phenylenebis(p-sulfonylaniline),
   p,p'-oxybis(p-phenylsulfonylaniline),
   p,p'-bis(p-phenylsulfonylaniline),
   1,5-naphthylenebis(p-sulfonylaniline).

The dinitro disulfones of the kind referred to above may be prepared by the interaction of a di-sodium arylenedisulfinate (1 mole) and a p-halonitrobenzene (2 moles), either the chloro- or the bromo-nitrobenzene being suitable. Sodium benzenedisulfinate or sodium toluenedisulfinate may be used.

The diamino disulfones may be prepared by reduction of the corresponding dinitro disulfones, as by means of stannous chloride, or by hydrogenation with the aid of a catalyst such as palladium on carbon.

Another method of preparing the diamino di-sulfones involves the reaction of two moles of sodium N-acetylaniline-p-sulfinate with one mole of a p-halonitrobenzene, followed by hydrolysis to remove the acetyl groups.

The known ditolyl arylene disulfones employed in my invention may be prepared either by the interaction of two moles of p-toluenesulfonyl chloride and one mole of an aromatic hydrocarbon or an aryl ether, such as biphenyl, or diphenyl ether, in the presence of a catalyst such as anhydrous ferric chloride; or by the interaction of sodium toluenesulfinate (2 moles) and one mole of chloro or bromo nitrobenzene.

The arylene disulfonyl dibenzoic acids may be made by oxidation of the corresponding ditolyl arylene disulfones by known methods, such as by the use of chromium trioxide in sulfuric and acetic acids.

These benzoic acids are converted to the corresponding benzoyl chlorides by known methods, as by the use of thionyl chloride.

The following examples illustrate the preparation of my new monomers.

EXAMPLE VII

This illustrates the preparation of bis[4-(4' nitrophenylsulfonyl)-phenyl] ether by the reaction of disodium 4,4'-oxydibenzenesulfinate hydrate with p-chloronitrobenzene.

To 200 ml. of commercial ethylene glycol in a reaction flask there was added 50 grams of disodium 4,4'-oxydibenzenesulfinate hydrate and 50 grams of p-chloronitrobenzene, and the mixture was heated at reflux for 5 hours, during which small quantities of water were added to maintain the refluxing temperature of the solution at 150–170°C. Then the reaction mixture was cooled and 200 ml. methanol was added to dissolve the unreacted p-chloronitrobenzene. After stirring for 30 minutes, the resulting precipitate was separated and washed with methanol several times, yielding 40 grams of a tan-colored product (50% yield). The product was further purified by dissolving it in hot tetrachloroethane and reprecipitating in methanol, resulting in a yellowish crystalline product having a melting point of 245–250°C.

Elemental analysis calculated for $C_{24}H_{16}N_2O_9S_2$: Found: C, 53.33; H, 2.98; N, 5.18; S, 11.86. C, 53.51; H, 3.18; N, 4.87; S, 11.34.

C, 53.52; H, 3.02; N, 4.89; S, 11.50.

EXAMPLE VIII

This illustrates the preparation of 4,4'-oxybis[p-(phenylsulfonylaniline)] by reduction of the dinitro product of Example VII by (a) catalytic hydrogenation and by (b) stannous chloride.

a. Thirteen grams (0.0025 mole) of the dinitro product of Example VII was weighed out and placed in a reaction flask containing 200 ml. of 2-methoxyethanol and 1.0 gram of 5% Pd/C. Reduction was initiated at room temperature using a Parr shaker, with hydrogen at 30 pounds pressure. The reaction was exothermic, and was essentially complete in 40 minutes. The yellowish solution was filtered, and dissolved in methyl alcohol/water mixture and reprecipitated with concentrated HCl, yielding a yellow, crystalline product.

b. Twenty-five grams of the dinitro product of Example VII was added to a reaction flask containing 250 ml. of methyl alcohol-concentrated HCl (50:50 by vol.) and 70 grams of stannous chloride dihydrate. The mixture was refluxed, with stirring, for 3 hours, at which time reduction was complete. The precipitated diamine dihydrochloride was then separated by filtration, and purification was carried out in the same manner as in (a) above, to yield a yellow, crystalline product.

Elemental analysis calculated for $C_{24}H_{20}S_2O_5N_2$: Found C, 59.98; H, 4.19; N, 5.83; S, 12.34. C, 59.32; H, 4.23; N, 5.76; S, 12.79.

C, 59.17; H, 4.23; N, 5.77; S, 12.82.

4,4'-Oxybis-(p-phenylsulfonyltoluene) may be prepared as follows:

In a 1000 ml. Erlenmeyer flask there was placed 80 g. (0.47 mole) of commercial anhydrous diphenyl ether and 179 g. (0.94 mole) of commercial p-toluenesulfonyl chloride. The mixture was warmed at 70'C., with stirring. Then was added about 2-3g. of anhydrous ferric chloride, and the mixture was slowly warmed to 120°C. The reaction started suddenly and hydrogen chloride was evolved vigorously.

When the temperature reached 130°C., the reaction mixture was removed from the hot plate and cooled to 80°C. The flask was then returned to the hot plate and heated to 120°C. The reaction mixture became very viscous. After stirring for an additional 30 minutes, the reaction mixture was cooled to room temperature.

To the reaction mixture was added 500 ml. of 95% ethanol, and the mixture was warmed to the boiling point (117°C.). The hard, glassy product became slowly dispersed and finally became finely divided. After stirring for an hour, the solid portion was separated by filtration. The solid was then washed with cold ethanol and recrystallized from hot toluene with a small amount of charcoal, yielding white crystals, m.p. 165°C.

Elemental analysis calculated for $C_{26}H_{22}O_5S_2$: Found: C, 65.25; H, 4.63; S, 13.4% C, 65.83; H, 4.67; S, 12.80
C, 65.74; H, 4.72; S, 12.68

4,4'-Oxybis-(p-phenylsulfonylbenzoic acid) may be prepared by oxidation of the product next above.

In a 4000 ml. beaker there was placed 500 ml. of water, 500 ml. of concentrated $H_2SO_4$ and 800 ml. of acetic acid. To it there was added 300 g. of chromium trioxide. The mixture was warmed to 70°C., with stirring. With continued stirring, 200 g. of 4,4'-oxybis(p-phenylsulfonyltoluene) in 1000 ml. of hot acetic acid was added slowly. Some gas evolved. During the addition the temperature was kept below 80°C. If the solution became completely green, more $CrO_3$ was added. After the completion of addition, the reaction mixture was stirred for an additional 30 minutes.

The reaction mixture was then cooled and the precipitated dicarboxylic acid was separated by filtration and washed repeatedly with water. The crystalline product was purified by reprecipitation from methoxyethanol with water; m.p., 325°–330°C.

Elemental analysis calculated for $C_{26}H_{18}O_9S_2$: Found: C, 57.99; H, 3.37; S, 11.91. C, 58.62; H, 3.60; S, 11.24.
C, 58.43; H, 3.40; S, 11.21.

p-Bis(p-tolylsulfonyl)benzene may be prepared as follows:

In a 500 ml. flask there was placed 200 ml. of dimethylsulfoxide, 50 g. of sodium p-toluenesulfinate dihydrate and 10 g. of p-bromonitrobenzene. The reaction mixture was heated at 130°C., with stirring, for 24 hours. The mixture was then poured into 2000 ml. of water. The precipitate was separated by filtration and was recrystallized from hot toluene, yielding white crystals, m.p. 239°C.

Elemental analysis calculated for $C_{20}H_{18}O_4S_2$: Found: C, 62.15; H, 4.69; S, 16.59. C, 62.06; H, 4.49; S, 15.86. C, 62.09; H, 4.79; S, 15.81.

4,4'-Oxybis(p-phenylsulfonylbenzoyl chloride) may be prepared as follows:

4,4'-Oxybis(p-phenylsulfonylbenzoic acid), 100 grams, was refluxed with an excess of thionyl chloride (500 ml.) in the presence of 1 ml. of pyridine as catalyst. Refluxing was continued until a homogeneous solution was obtained. After removing the excess thionyl chloride, using vacuum, the solution was recrystallized from hot toluene, yielding a white, crystalline product of needle-like structure; melting point, 220°–222°C.

I claim:

1. A bis (nitrophenylsulfonyl) arylene compound having the formula:

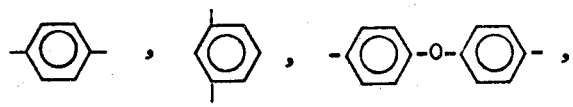

wherein R' is selected from the group consisting of

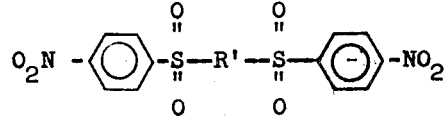 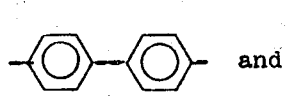 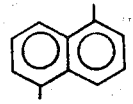

2. A compound according to claim 1 which is bis[4-(4'-nitrophenylsulfonyl)phenyl] ether.

3. A bis (aminophenylsulfonyl) arylene compound having the formula:

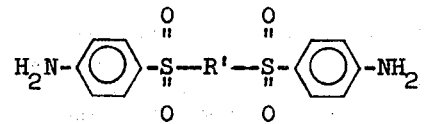

wherein R' is selected from the group consisting of

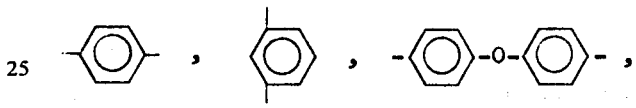

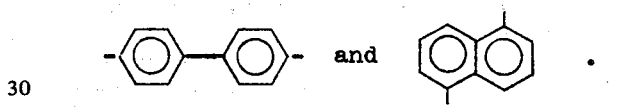

4. A compound according to claim 3 which is 4,4'-oxybis(phenylsulfonylaniline).

* * * * *